United States Patent
Goodnow et al.

(10) Patent No.: US 8,460,243 B2
(45) Date of Patent: Jun. 11, 2013

(54) GLUCOSE MEASURING MODULE AND INSULIN PUMP COMBINATION

(75) Inventors: Timothy T. Goodnow, Pleasanton, CA (US); Michael L. Blomquist, Blaine, MN (US); Jay G. Johnson, Maple Plain, MN (US)

(73) Assignees: Abbott Diabetes Care Inc., Alameda, CA (US); Deltec, Inc., St. Paul, MN (US)

(*) Notice: Subject to any disclaimer, the term of this patent is extended or adjusted under 35 U.S.C. 154(b) by 963 days.

(21) Appl. No.: 10/458,914

(22) Filed: Jun. 10, 2003

(65) Prior Publication Data

US 2004/0254434 A1    Dec. 16, 2004

(51) Int. Cl.
*A61M 37/00*    (2006.01)

(52) U.S. Cl.
USPC .......................................... 604/131; 604/890.1

(58) Field of Classification Search
USPC ........................ 600/365; 604/131, 504, 66, 67
See application file for complete search history.

(56) References Cited

U.S. PATENT DOCUMENTS

| | | | |
|---|---|---|---|
| 3,956,701 A | 5/1976 | James, Jr. et al. | |
| 4,432,360 A | 2/1984 | Mumford et al. | |
| 4,558,139 A | 12/1985 | Hagenmaier et al. | |
| 4,559,037 A | 12/1985 | Franetzki et al. | |
| 4,619,995 A | 10/1986 | Hayes | |
| 4,635,836 A | 1/1987 | Mooney et al. | |
| 4,703,756 A | 11/1987 | Gough et al. | |
| 4,731,726 A | 3/1988 | Allen | |
| 5,016,326 A | 5/1991 | Goldenberg | |
| 5,019,974 A | 5/1991 | Beckers | |
| 5,054,170 A | 10/1991 | Otrusina | |
| 5,127,404 A | 7/1992 | Wyborny et al. | |
| 5,216,597 A | 6/1993 | Beckers | |
| 5,251,126 A | 10/1993 | Kahn et al. | |
| 5,261,583 A | 11/1993 | Long et al. | |
| 5,276,628 A | 1/1994 | Schneiderhan | |
| 5,304,468 A | 4/1994 | Phillips et al. | |
| 5,307,263 A | 4/1994 | Brown | |

(Continued)

FOREIGN PATENT DOCUMENTS

| | | |
|---|---|---|
| EP | 1372102 | 12/2003 |
| JP | 2002-126092 | 5/2002 |

(Continued)

OTHER PUBLICATIONS

International Search Report and Written Opinion of the International Searching Authority for PCT Application No. PCT/US2004/018204 filed Jun. 4, 2004.

(Continued)

*Primary Examiner* — Kevin C Sirmons
*Assistant Examiner* — Phillip Gray
(74) *Attorney, Agent, or Firm* — Jackson & Co., LLP

(57) ABSTRACT

A combination glucose measuring and insulin pumping device is described. The two major components, a glucose measuring module and an insulin pump, are held together by a quick attach and release mechanism. Communication between the glucose measuring module and the insulin pump is by a wireless modality. The glucose measuring module determines the glucose level in a sample, and wirelessly transmits the data to the insulin pump, where the data are stored in a memory, and are available for visual display on the insulin pump, and for incorporation into selection of appropriate protocols for the rate of insulin infusion by the pump into the patient.

19 Claims, 3 Drawing Sheets

U.S. PATENT DOCUMENTS

| | | | |
|---|---|---|---|
| 5,319,543 A | 6/1994 | Wilhelm | |
| 5,349,852 A | 9/1994 | Kamen et al. | |
| 5,360,446 A | 11/1994 | Kennedy | |
| 5,376,070 A * | 12/1994 | Purvis et al. | 604/31 |
| 5,385,282 A | 1/1995 | Chen | |
| 5,426,825 A | 6/1995 | Soren et al. | |
| 5,437,024 A | 7/1995 | French | |
| 5,452,829 A | 9/1995 | King et al. | |
| 5,472,317 A * | 12/1995 | Field et al. | 417/234 |
| 5,489,414 A | 2/1996 | Schreiber et al. | |
| 5,492,117 A | 2/1996 | Eisenberg et al. | |
| 5,526,844 A | 6/1996 | Kamen et al. | |
| 5,528,770 A | 6/1996 | Castilla et al. | |
| 5,533,389 A | 7/1996 | Kamen et al. | |
| 5,542,024 A | 7/1996 | Balint | |
| 5,544,044 A | 8/1996 | Leathernman | |
| 5,558,638 A | 9/1996 | Evers et al. | |
| 5,562,713 A | 10/1996 | Silvian | |
| 5,563,042 A | 10/1996 | Phillips et al. | |
| 5,594,637 A | 1/1997 | Eisenberg et al. | |
| 5,597,102 A | 1/1997 | Saarikko et al. | |
| 5,601,435 A | 2/1997 | Quy | |
| 5,613,236 A | 3/1997 | Tajima et al. | |
| 5,620,120 A | 4/1997 | Tien | |
| 5,622,296 A | 4/1997 | Pirhonen et al. | |
| 5,626,630 A | 5/1997 | Markowitz et al. | |
| 5,665,065 A | 9/1997 | Colman et al. | |
| 5,678,571 A | 10/1997 | Brown | |
| 5,683,407 A | 11/1997 | Jolly et al. | |
| 5,683,432 A | 11/1997 | Goedeke et al. | |
| 5,691,486 A | 11/1997 | Behringer | |
| 5,696,686 A | 12/1997 | Sanka et al. | |
| 5,719,667 A | 2/1998 | Miers | |
| 5,730,342 A | 3/1998 | Tien | |
| D393,313 S | 4/1998 | Meisner et al. | |
| 5,735,285 A | 4/1998 | Albert et al. | |
| 5,741,289 A | 4/1998 | Jolly et al. | |
| 5,745,308 A | 4/1998 | Spangenberg | |
| 5,749,907 A | 5/1998 | Mann | |
| 5,752,976 A | 5/1998 | Duffin et al. | |
| 5,772,586 A | 6/1998 | Heinonen et al. | |
| 5,772,963 A | 6/1998 | Cantatore et al. | |
| 5,788,927 A | 8/1998 | Farrell et al. | |
| 5,791,344 A | 8/1998 | Schulman et al. | |
| 5,792,204 A | 8/1998 | Snell | |
| 5,800,473 A | 9/1998 | Faisandier | |
| 5,822,715 A | 10/1998 | Worthington et al. | |
| 5,843,692 A | 12/1998 | Phillips et al. | |
| 5,844,685 A | 12/1998 | Gontin | |
| 5,848,137 A | 12/1998 | Hsiao | |
| 5,861,019 A | 1/1999 | Sun et al. | |
| 5,872,627 A | 2/1999 | Miers | |
| 5,883,378 A | 3/1999 | Irish et al. | |
| 5,897,493 A | 4/1999 | Brown | |
| 5,899,855 A | 5/1999 | Brown | |
| 5,906,031 A | 5/1999 | Jensen | |
| 5,907,796 A | 5/1999 | Matchett et al. | |
| 5,908,599 A | 6/1999 | Behringer et al. | |
| 5,912,114 A | 6/1999 | Hutchinson et al. | |
| 5,913,310 A | 6/1999 | Brown | |
| 5,916,501 A | 6/1999 | Hehl | |
| 5,918,603 A | 7/1999 | Brown | |
| 5,933,136 A | 8/1999 | Brown | |
| 5,934,885 A | 8/1999 | Farrell et al. | |
| 5,936,986 A | 8/1999 | Cantatore et al. | |
| 5,939,583 A | 8/1999 | Kluender et al. | |
| 5,940,802 A | 8/1999 | Hildebrand et al. | |
| 5,951,300 A | 9/1999 | Brown | |
| 5,953,681 A | 9/1999 | Cantatore et al. | |
| 5,956,501 A | 9/1999 | Brown | |
| 5,960,403 A | 9/1999 | Brown | |
| 5,961,451 A | 10/1999 | Reber et al. | |
| 5,968,760 A | 10/1999 | Phillips et al. | |
| 5,968,764 A | 10/1999 | Knowles et al. | |
| 5,972,680 A | 10/1999 | Knowles et al. | |
| 5,973,842 A | 10/1999 | Spangenberg | |
| 5,988,577 A | 11/1999 | Phillips et al. | |
| 5,994,295 A | 11/1999 | Khoo et al. | |
| 5,997,475 A | 12/1999 | Bortz | |
| 5,997,476 A | 12/1999 | Brown | |
| 5,999,857 A | 12/1999 | Weijand et al. | |
| 6,014,629 A | 1/2000 | DeBruin-Ashton | |
| 6,024,699 A | 2/2000 | Surwit et al. | |
| 6,032,337 A | 3/2000 | Rankin, Jr. et al. | |
| 6,042,249 A | 3/2000 | Spangenberg | |
| 6,048,900 A | 4/2000 | Connell et al. | |
| 6,083,248 A | 7/2000 | Thompson | |
| 6,088,618 A | 7/2000 | Kerver | |
| 6,101,478 A | 8/2000 | Brown | |
| 6,125,513 A | 10/2000 | Cheraso et al. | |
| 6,128,620 A | 10/2000 | Pissanos et al. | |
| 6,139,494 A | 10/2000 | Cairnes | |
| 6,150,951 A | 11/2000 | Olejniczak | |
| 6,151,586 A | 11/2000 | Brown | |
| 6,159,147 A | 12/2000 | Lichter et al. | |
| 6,161,095 A | 12/2000 | Brown | |
| 6,167,362 A | 12/2000 | Brown et al. | |
| 6,168,563 B1 | 1/2001 | Brown | |
| 6,175,752 B1 | 1/2001 | Say et al. | |
| 6,177,940 B1 | 1/2001 | Bond et al. | |
| 6,186,145 B1 | 2/2001 | Brown | |
| 6,188,648 B1 | 2/2001 | Olsen | |
| 6,190,324 B1 | 2/2001 | Kieval et al. | |
| 6,233,301 B1 | 5/2001 | Robergeau | |
| 6,233,539 B1 | 5/2001 | Brown | |
| 6,238,337 B1 | 5/2001 | Kambhatla et al. | |
| 6,240,393 B1 | 5/2001 | Brown | |
| 6,242,463 B1 | 6/2001 | Reitberg | |
| 6,243,606 B1 | 6/2001 | Mann et al. | |
| 6,248,065 B1 | 6/2001 | Brown | |
| 6,248,067 B1 | 6/2001 | Causey, III et al. | |
| 6,249,705 B1 | 6/2001 | Snell | |
| 6,259,950 B1 | 7/2001 | Mann et al. | |
| 6,263,244 B1 | 7/2001 | Mann et al. | |
| 6,268,162 B1 | 7/2001 | Phillips et al. | |
| 6,269,276 B1 | 7/2001 | Akhavan et al. | |
| 6,270,455 B1 | 8/2001 | Brown | |
| 6,283,348 B1 | 9/2001 | Wang | |
| 6,283,761 B1 | 9/2001 | Joao | |
| 6,285,377 B1 | 9/2001 | Greenbaum et al. | |
| 6,285,908 B1 | 9/2001 | Mann et al. | |
| 6,311,089 B1 | 10/2001 | Mann et al. | |
| 6,322,504 B1 | 11/2001 | Kirshner | |
| 6,327,501 B1 | 12/2001 | Levine et al. | |
| 6,330,426 B2 | 12/2001 | Brown et al. | |
| 6,348,640 B1 | 2/2002 | Navot et al. | |
| 6,352,505 B1 | 3/2002 | Bortz | |
| 6,359,444 B1 | 3/2002 | Grimes | |
| 6,368,273 B1 | 4/2002 | Brown | |
| 6,375,469 B1 | 4/2002 | Brown | |
| 6,379,301 B1 | 4/2002 | Worthington et al. | |
| 6,381,577 B1 | 4/2002 | Brown | |
| 6,396,416 B1 | 5/2002 | Kuusela et al. | |
| 6,410,792 B1 | 6/2002 | Connell et al. | |
| 6,418,346 B1 | 7/2002 | Nelson et al. | |
| 6,426,502 B1 | 7/2002 | Finarov | |
| 6,428,475 B1 | 8/2002 | Shen | |
| 6,434,429 B1 | 8/2002 | Kraus et al. | |
| 6,438,229 B1 | 8/2002 | Overy et al. | |
| 6,442,432 B2 | 8/2002 | Lee | |
| 6,443,340 B1 | 9/2002 | Chung et al. | |
| 6,454,708 B1 | 9/2002 | Ferguson et al. | |
| 6,470,215 B1 | 10/2002 | Kraus et al. | |
| 6,470,320 B1 | 10/2002 | Hildebrand et al. | |
| 6,470,535 B1 | 10/2002 | Mayne et al. | |
| 6,477,424 B1 | 11/2002 | Thompson et al. | |
| 6,485,461 B1 | 11/2002 | Mason et al. | |
| 6,489,133 B2 | 12/2002 | Phillips et al. | |
| 6,490,487 B1 | 12/2002 | Kraus et al. | |
| 6,497,655 B1 | 12/2002 | Linberg et al. | |
| 6,512,942 B1 | 1/2003 | Burdette et al. | |
| 6,518,069 B1 | 2/2003 | Otvos et al. | |
| 6,525,330 B2 | 2/2003 | Paolini et al. | |
| 6,529,841 B2 | 3/2003 | Cocking et al. | |
| 6,540,672 B1 | 4/2003 | Simonsen et al. | |
| 6,541,266 B2 | 4/2003 | Modzelewski et al. | |
| 6,549,796 B2 | 4/2003 | Sohrab | |

| Patent | Date | Inventor |
|---|---|---|
| 6,551,276 B1 | 4/2003 | Mann et al. |
| 6,554,798 B1 | 4/2003 | Mann et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,625 B2 | 5/2003 | Modzelewski et al. |
| 6,564,105 B2 | 5/2003 | Starkweather et al. |
| 6,571,128 B2 | 5/2003 | Lebel et al. |
| 6,574,510 B2 | 6/2003 | Von Arx et al. |
| 6,579,888 B2 | 6/2003 | Reitberg |
| 6,582,365 B1 | 6/2003 | Hines et al. |
| 6,582,366 B1 | 6/2003 | Porumbescu |
| 6,583,108 B1 | 6/2003 | Tamburini et al. |
| 6,584,335 B1 | 6/2003 | Haar et al. |
| 6,585,644 B2 | 7/2003 | Lebel et al. |
| 6,594,523 B1 | 7/2003 | Levine |
| 6,599,250 B2 | 7/2003 | Webb et al. |
| 6,602,191 B2 | 8/2003 | Quy |
| 6,602,469 B1 | 8/2003 | Maus et al. |
| 6,604,050 B2 | 8/2003 | Trippel et al. |
| 6,609,032 B1 | 8/2003 | Woods et al. |
| 6,613,942 B1 | 9/2003 | Ling et al. |
| 6,618,622 B1 | 9/2003 | Mann et al. |
| 6,633,772 B2 | 10/2003 | Ford et al. |
| 6,641,353 B2 | 11/2003 | Oliver |
| 6,641,533 B2 | 11/2003 | Causey, III et al. |
| 6,644,322 B2 | 11/2003 | Webb |
| 6,645,142 B2 | 11/2003 | Braig et al. |
| 6,648,821 B2 | 11/2003 | Lebel et al. |
| 6,656,114 B1 | 12/2003 | Poulsen et al. |
| 6,656,158 B2 | 12/2003 | Mahoney et al. |
| 6,656,159 B2 | 12/2003 | Flaherty |
| 6,658,456 B1 | 12/2003 | Shimoosawa |
| 6,659,948 B2 | 12/2003 | Lebel et al. |
| 6,665,909 B2 | 12/2003 | Collins et al. |
| 6,669,669 B2 | 12/2003 | Flaherty et al. |
| 6,675,044 B2 | 1/2004 | Chen |
| 6,687,546 B2 | 2/2004 | Lebel et al. |
| 6,692,457 B2 | 2/2004 | Flaherty |
| 6,694,191 B2 | 2/2004 | Starkweather et al. |
| 6,699,218 B2 | 3/2004 | Flaherty et al. |
| 6,702,857 B2 | 3/2004 | Brauker et al. |
| 6,723,046 B2 | 4/2004 | Lichtenstein et al. |
| 6,723,072 B2 | 4/2004 | Flaherty et al. |
| 6,731,976 B2 | 5/2004 | Penn et al. |
| 6,733,446 B2 | 5/2004 | Lebel et al. |
| 6,733,619 B2 | 5/2004 | Finarov |
| 6,740,059 B2 | 5/2004 | Flaherty |
| 6,741,877 B1 | 5/2004 | Shults et al. |
| 6,744,350 B2 | 6/2004 | Blomquist |
| 6,748,250 B1 | 6/2004 | Berman et al. |
| 6,749,587 B2 | 6/2004 | Flaherty |
| 6,752,299 B2 | 6/2004 | Shetler et al. |
| 6,766,198 B1 | 7/2004 | Snell |
| 6,766,201 B2 | 7/2004 | Von Arx et al. |
| 6,768,425 B2 | 7/2004 | Flaherty et al. |
| 6,772,026 B2 | 8/2004 | Bradbury et al. |
| 6,781,522 B2 | 8/2004 | Sleva et al. |
| 6,786,405 B2 | 9/2004 | Wiedenhoefer |
| 6,791,686 B1 | 9/2004 | Finarov |
| 6,793,632 B2 | 9/2004 | Sohrab |
| 6,802,810 B2 | 10/2004 | Ciarniello et al. |
| 6,804,558 B2 | 10/2004 | Haller et al. |
| 6,804,656 B1 | 10/2004 | Rosenfeld et al. |
| 6,809,653 B1 | 10/2004 | Mann et al. |
| 6,811,516 B1 | 11/2004 | Dugan |
| 6,811,533 B2 | 11/2004 | Lebel et al. |
| 6,814,845 B2 | 11/2004 | Wilson et al. |
| 6,820,235 B1 | 11/2004 | Bleicher et al. |
| 6,821,483 B2 | 11/2004 | Phillips et al. |
| 6,825,933 B2 | 11/2004 | Roberts et al. |
| 6,830,558 B2 | 12/2004 | Flaherty et al. |
| 6,835,381 B1 | 12/2004 | Friedrich et al. |
| 6,847,451 B2 | 1/2005 | Pugh |
| 6,849,237 B2 | 2/2005 | Housefield et al. |
| 6,852,104 B2 | 2/2005 | Blomquist |
| 6,856,928 B2 | 2/2005 | Harmon |
| 6,858,401 B2 | 2/2005 | Phillips et al. |
| 6,862,465 B2 | 3/2005 | Shults et al. |
| 6,862,466 B2 | 3/2005 | Ackerman |
| 6,865,515 B2 | 3/2005 | Fox et al. |
| 6,878,112 B2 | 4/2005 | Linberg et al. |
| 6,913,174 B1 | 7/2005 | Harvey et al. |
| 6,916,159 B2 | 7/2005 | Rush et al. |
| 6,925,393 B1 | 8/2005 | Kalatz et al. |
| 6,931,327 B2 | 8/2005 | Goode, Jr. et al. |
| 6,936,007 B2 | 8/2005 | Quy |
| 6,939,310 B2 | 9/2005 | Matzinger et al. |
| 6,941,163 B2 | 9/2005 | Ford et al. |
| 6,942,518 B2 | 9/2005 | Liamos et al. |
| 6,943,787 B2 | 9/2005 | Webb |
| 6,946,299 B2 | 9/2005 | Neel et al. |
| 6,954,673 B2 | 10/2005 | Von Arx et al. |
| 6,957,102 B2 | 10/2005 | Silver et al. |
| 6,957,107 B2 | 10/2005 | Rogers et al. |
| 6,960,192 B1 | 11/2005 | Flaherty et al. |
| 6,961,448 B2 | 11/2005 | Nichols et al. |
| 6,964,871 B2 | 11/2005 | Bell et al. |
| 6,968,375 B1 | 11/2005 | Brown |
| 6,974,328 B2 | 12/2005 | Aspe et al. |
| 6,976,958 B2 | 12/2005 | Quy |
| 6,978,182 B2 | 12/2005 | Mazar et al. |
| 6,978,517 B2 | 12/2005 | Collins et al. |
| 6,980,958 B1 | 12/2005 | Surwit et al. |
| 6,980,999 B1 | 12/2005 | Grana |
| 6,984,307 B2 | 1/2006 | Zweig |
| 6,985,088 B2 | 1/2006 | Goetz et al. |
| 6,999,816 B2 | 2/2006 | Van Bentem |
| 7,003,335 B2 | 2/2006 | Briancon |
| 7,011,425 B2 | 3/2006 | Morris et al. |
| 7,011,630 B2 | 3/2006 | Desai et al. |
| 7,018,360 B2 | 3/2006 | Flaherty et al. |
| 7,018,568 B2 | 3/2006 | Tierney |
| 7,019,123 B2 | 3/2006 | Tamburini et al. |
| 7,020,515 B2 | 3/2006 | Graindorge |
| 7,022,072 B2 | 4/2006 | Fox et al. |
| 7,023,359 B2 | 4/2006 | Goetz et al. |
| 7,024,236 B2 | 4/2006 | Ford et al. |
| 7,029,455 B2 | 4/2006 | Flaherty |
| 7,039,810 B1 | 5/2006 | Nichols |
| 7,041,468 B2 | 5/2006 | Drucker et al. |
| 7,049,962 B2 | 5/2006 | Atherton et al. |
| 7,050,855 B2 | 5/2006 | Zeijlemaker et al. |
| 7,052,251 B2 | 5/2006 | Nason et al. |
| 7,058,453 B2 | 6/2006 | Nelson et al. |
| 7,060,031 B2 | 6/2006 | Webb et al. |
| 7,069,085 B2 | 6/2006 | Cao et al. |
| 7,070,564 B2 | 7/2006 | Matzinger et al. |
| 7,072,725 B2 | 7/2006 | Bristol et al. |
| 7,074,307 B2 | 7/2006 | Simpson et al. |
| 7,076,520 B2 | 7/2006 | Nelson et al. |
| 7,077,806 B2 | 7/2006 | Ackermann et al. |
| 7,081,195 B2 | 7/2006 | Simpson et al. |
| 7,082,334 B2 | 7/2006 | Boute et al. |
| 7,089,049 B2 | 8/2006 | Kerver et al. |
| 7,092,891 B2 | 8/2006 | Maus et al. |
| 7,103,414 B1 | 9/2006 | Poore et al. |
| 7,103,578 B2 | 9/2006 | Beck et al. |
| 7,107,547 B2 | 9/2006 | Cule et al. |
| 7,108,778 B2 | 9/2006 | Simpson et al. |
| 7,110,803 B2 | 9/2006 | Shults et al. |
| 7,113,172 B2 | 9/2006 | Hohl et al. |
| 7,125,382 B2 | 10/2006 | Zhou et al. |
| 7,127,299 B2 | 10/2006 | Nelson et al. |
| 7,129,744 B2 | 10/2006 | Madurawe |
| 7,134,999 B2 | 11/2006 | Brauker et al. |
| 7,136,689 B2 | 11/2006 | Shults et al. |
| 7,137,951 B2 | 11/2006 | Pilarski |
| 7,137,964 B2 | 11/2006 | Flaherty |
| 7,141,548 B2 | 11/2006 | Johansen et al. |
| 7,144,384 B2 | 12/2006 | Gorman et al. |
| 7,149,773 B2 | 12/2006 | Haller et al. |
| 7,150,975 B2 | 12/2006 | Tamada et al. |
| 7,155,290 B2 | 12/2006 | Von Arx et al. |
| 7,156,655 B2 | 1/2007 | Sachdeva et al. |
| 7,156,808 B2 | 1/2007 | Quy |
| 7,156,809 B2 | 1/2007 | Quy |

| Patent No. | Date | Inventor |
|---|---|---|
| 7,160,251 B2 | 1/2007 | Neel et al. |
| 7,167,818 B2 | 1/2007 | Brown |
| 7,172,890 B2 | 2/2007 | Shao et al. |
| 7,173,005 B2 | 2/2007 | Pillutla et al. |
| 7,179,226 B2 | 2/2007 | Crothall et al. |
| 7,181,505 B2 | 2/2007 | Haller et al. |
| 7,183,068 B2 | 2/2007 | Burson et al. |
| 7,189,341 B2 | 3/2007 | Li et al. |
| 7,192,450 B2 | 3/2007 | Brauker et al. |
| 7,202,854 B2 | 4/2007 | Hohl et al. |
| 7,204,823 B2 | 4/2007 | Estes et al. |
| 7,226,278 B2 | 6/2007 | Nason et al. |
| 7,226,978 B2 | 6/2007 | Tapsak et al. |
| 7,228,163 B2 | 6/2007 | Ackerman |
| 7,229,288 B2 | 6/2007 | Stuart et al. |
| 7,231,263 B2 | 6/2007 | Choi |
| 7,232,451 B2 | 6/2007 | Boecker et al. |
| 7,234,937 B2 | 6/2007 | Sachdeva et al. |
| 7,236,826 B2 | 6/2007 | Lindh et al. |
| 7,245,117 B1 | 7/2007 | Joy et al. |
| 7,255,748 B2 | 8/2007 | Finarov |
| 7,258,673 B2 | 8/2007 | Racchini et al. |
| 7,259,681 B2 | 8/2007 | Kwoen |
| 7,261,690 B2 | 8/2007 | Teller et al. |
| 7,261,691 B1 | 8/2007 | Asomani |
| 7,267,651 B2 | 9/2007 | Nelson |
| 7,276,029 B2 | 10/2007 | Goode, Jr. et al. |
| 7,278,983 B2 | 10/2007 | Ireland et al. |
| 7,282,029 B1 | 10/2007 | Poulsen et al. |
| 7,288,736 B2 | 10/2007 | Schildgen |
| 7,295,988 B1 | 11/2007 | Reeves |
| 7,303,549 B2 | 12/2007 | Flaherty et al. |
| 7,306,562 B1 | 12/2007 | Baykal |
| 7,310,544 B2 | 12/2007 | Brister et al. |
| 7,310,651 B2 | 12/2007 | Dave et al. |
| 7,319,107 B2 | 1/2008 | Eisinger et al. |
| 7,323,296 B2 | 1/2008 | Ma et al. |
| 7,324,012 B2 | 1/2008 | Mann et al. |
| 7,324,949 B2 | 1/2008 | Bristol |
| 7,325,076 B1 | 1/2008 | Morrison et al. |
| 7,347,836 B2 | 3/2008 | Peterson et al. |
| 7,348,500 B2 | 3/2008 | Zhou |
| 7,349,947 B1 | 3/2008 | Slage et al. |
| 7,353,179 B2 | 4/2008 | Ott et al. |
| 7,354,420 B2 | 4/2008 | Steil et al. |
| 7,358,238 B2 | 4/2008 | Andersen et al. |
| 7,361,143 B2 | 4/2008 | Kirchhoff et al. |
| 7,364,592 B2 | 4/2008 | Carr-Brendel et al. |
| 7,366,556 B2 | 4/2008 | Brister et al. |
| 7,378,494 B2 | 5/2008 | Froland et al. |
| 7,379,765 B2 | 5/2008 | Petisce et al. |
| 7,384,397 B2 | 6/2008 | Zhang et al. |
| 7,384,967 B2 | 6/2008 | Polisetti et al. |
| 7,390,484 B2 | 6/2008 | Fraser et al. |
| 7,395,117 B2 | 7/2008 | Mazar et al. |
| 7,395,216 B2 | 7/2008 | Rosenfeld et al. |
| 7,396,330 B2 | 7/2008 | Banet et al. |
| 7,399,277 B2 | 7/2008 | Saidara et al. |
| 7,403,814 B2 | 7/2008 | Cox et al. |
| 7,424,318 B2 | 9/2008 | Brister et al. |
| 7,433,827 B2 | 10/2008 | Rosenfeld et al. |
| 7,436,532 B2 | 10/2008 | Tsujimoto |
| 7,445,152 B2 | 11/2008 | Golabek, Jr. et al. |
| 7,447,596 B2 | 11/2008 | Kawatahara et al. |
| 7,454,359 B2 | 11/2008 | Rosenfeld et al. |
| 7,460,898 B2 | 12/2008 | Brister et al. |
| 7,463,930 B2 | 12/2008 | Housworth et al. |
| 7,464,041 B2 | 12/2008 | Merkin et al. |
| 7,467,003 B2 | 12/2008 | Brister et al. |
| 7,468,125 B2 | 12/2008 | Kraft et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,504,233 B2 | 3/2009 | Hellerstein |
| 7,515,060 B2 | 4/2009 | Blomquist |
| 7,516,847 B2 | 4/2009 | Henning |
| 7,517,664 B2 | 4/2009 | Shao et al. |
| 7,519,408 B2 | 4/2009 | Rasdal et al. |
| 7,519,478 B2 | 4/2009 | Bartkowiak et al. |
| 7,523,004 B2 | 4/2009 | Bartkowiak et al. |
| 7,539,532 B2 | 5/2009 | Tran |
| 7,539,533 B2 | 5/2009 | Tran |
| 7,541,373 B2 | 6/2009 | Polisetti et al. |
| 7,551,175 B2 | 6/2009 | Sakanishi et al. |
| 7,551,301 B2 | 6/2009 | Yamaguchi et al. |
| 7,552,101 B2 | 6/2009 | Bleines |
| 7,563,232 B2 | 7/2009 | Freeman et al. |
| 7,565,197 B2 | 7/2009 | Haubrich et al. |
| 7,574,266 B2 | 8/2009 | Dudding et al. |
| 7,575,457 B2 | 8/2009 | Micinski |
| 7,580,334 B2 | 8/2009 | Kadowaki et al. |
| 7,583,578 B2 | 9/2009 | Kadowaki et al. |
| 7,583,990 B2 | 9/2009 | Goode, Jr. et al. |
| 7,590,462 B2 | 9/2009 | Rubbert et al. |
| 7,591,801 B2 | 9/2009 | Brauker et al. |
| 7,593,952 B2 | 9/2009 | Soll et al. |
| 7,595,647 B2 | 9/2009 | Kroh et al. |
| 7,595,902 B2 | 9/2009 | Yamaguchi et al. |
| 7,599,726 B2 | 10/2009 | Goode, Jr. et al. |
| 7,600,022 B2 | 10/2009 | Takamine |
| 7,602,310 B2 | 10/2009 | Mann et al. |
| 7,604,593 B2 | 10/2009 | Parris et al. |
| 7,608,940 B2 | 10/2009 | Osawa |
| 7,613,491 B2 | 11/2009 | Boock et al. |
| 7,613,620 B2 | 11/2009 | Salwan |
| 7,615,007 B2 | 11/2009 | Shults et al. |
| 7,632,228 B2 | 12/2009 | Brauker et al. |
| 7,634,315 B2 | 12/2009 | Cholette |
| 7,637,868 B2 | 12/2009 | Saint et al. |
| 7,640,048 B2 | 12/2009 | Dobbles et al. |
| 7,643,969 B2 | 1/2010 | Soto et al. |
| 7,647,237 B2 | 1/2010 | Malave et al. |
| 7,651,489 B2 | 1/2010 | Estes et al. |
| 7,651,596 B2 | 1/2010 | Petisce et al. |
| 7,654,127 B2 | 2/2010 | Krulevitch et al. |
| 7,654,956 B2 | 2/2010 | Brister et al. |
| 7,654,976 B2 | 2/2010 | Peterson et al. |
| 7,657,297 B2 | 2/2010 | Simpson et al. |
| 7,657,442 B2 | 2/2010 | Merkin |
| 7,678,811 B2 | 3/2010 | Dumas et al. |
| 7,679,789 B2 | 3/2010 | Fukuda |
| 7,685,000 B1 | 3/2010 | Petit et al. |
| 7,697,152 B2 | 4/2010 | Hisatomi et al. |
| 7,698,117 B2 | 4/2010 | Usuka et al. |
| 7,699,775 B2 | 4/2010 | Desai et al. |
| 7,701,353 B1 | 4/2010 | Moreno |
| 7,705,653 B2 | 4/2010 | Schell |
| 7,705,980 B2 | 4/2010 | Smous et al. |
| 7,711,402 B2 | 5/2010 | Shults et al. |
| 7,713,574 B2 | 5/2010 | Brister et al. |
| 7,715,893 B2 | 5/2010 | Kamath et al. |
| 2001/0011221 A1 | 8/2001 | Underwood |
| 2001/0011224 A1 | 8/2001 | Brown |
| 2001/0025189 A1 | 9/2001 | Haueter et al. |
| 2001/0039504 A1 | 11/2001 | Linberg et al. |
| 2001/0054217 A1 | 12/2001 | Wang |
| 2002/0026111 A1 | 2/2002 | Ackerman |
| 2002/0029157 A1 | 3/2002 | Marchosky |
| 2002/0049617 A1 | 4/2002 | Lencki et al. |
| 2002/0055855 A1 | 5/2002 | Cule et al. |
| 2002/0072858 A1 | 6/2002 | Cheng |
| 2002/0082850 A1 | 6/2002 | Panelli |
| 2002/0107476 A1 | 8/2002 | Mann et al. |
| 2002/0128594 A1* | 9/2002 | Das et al. .................. 604/67 |
| 2002/0170148 A1 | 11/2002 | Mayne et al. |
| 2002/0188424 A1 | 12/2002 | Grinstein et al. |
| 2003/0023317 A1 | 1/2003 | Brauker et al. |
| 2003/0023461 A1 | 1/2003 | Quintanilla et al. |
| 2003/0032077 A1 | 2/2003 | Itoh et al. |
| 2003/0032867 A1 | 2/2003 | Crothall et al. |
| 2003/0032874 A1 | 2/2003 | Rhodes et al. |
| 2003/0040661 A1 | 2/2003 | Abraham et al. |
| 2003/0040821 A1 | 2/2003 | Case |
| 2003/0047575 A1 | 3/2003 | Enkerlin et al. |
| 2003/0055679 A1 | 3/2003 | Soll et al. |
| 2003/0058245 A1 | 3/2003 | Brazhnik et al. |
| 2003/0063524 A1 | 4/2003 | Niemiec et al. |
| 2003/0065534 A1 | 4/2003 | McCartney |

| Publication No. | Date | Inventor |
|---|---|---|
| 2003/0069753 A1 | 4/2003 | Brown |
| 2003/0078481 A1 | 4/2003 | McIvor et al. |
| 2003/0088238 A1* | 5/2003 | Poulsen et al. ............ 604/890.1 |
| 2003/0097279 A1 | 5/2003 | deLusignan et al. |
| 2003/0106917 A1 | 6/2003 | Shetler et al. |
| 2003/0110059 A1 | 6/2003 | Janes et al. |
| 2003/0120516 A1 | 6/2003 | Perednia |
| 2003/0158707 A1 | 8/2003 | Doi |
| 2003/0158754 A1 | 8/2003 | Elkind |
| 2003/0163351 A1 | 8/2003 | Brown et al. |
| 2003/0176183 A1 | 9/2003 | Drucker et al. |
| 2003/0176933 A1 | 9/2003 | Lebel et al. |
| 2003/0199739 A1 | 10/2003 | Gordon et al. |
| 2003/0208110 A1 | 11/2003 | Mault et al. |
| 2003/0208113 A1 | 11/2003 | Mault et al. |
| 2003/0212379 A1* | 11/2003 | Bylund et al. ................ 604/504 |
| 2003/0217966 A1 | 11/2003 | Tapsak et al. |
| 2003/0225324 A1 | 12/2003 | Anderson et al. |
| 2003/0229514 A2 | 12/2003 | Brown |
| 2003/0231552 A1* | 12/2003 | Markart .......................... 368/10 |
| 2004/0011671 A1 | 1/2004 | Shults et al. |
| 2004/0014069 A1 | 1/2004 | Cohen et al. |
| 2004/0035897 A1 | 2/2004 | Salentine et al. |
| 2004/0044548 A1 | 3/2004 | Marshall et al. |
| 2004/0045879 A1 | 3/2004 | Shults et al. |
| 2004/0054263 A1 | 3/2004 | Moerman et al. |
| 2004/0056055 A1 | 3/2004 | Folmer |
| 2004/0122353 A1* | 6/2004 | Shahmirian et al. ............ 604/65 |
| 2004/0133462 A1 | 7/2004 | Smith et al. |
| 2004/0135684 A1 | 7/2004 | Steinthal et al. |
| 2004/0152961 A1 | 8/2004 | Carlson et al. |
| 2004/0155079 A1 | 8/2004 | Shetler et al. |
| 2004/0165211 A1 | 8/2004 | Herrmann et al. |
| 2004/0172284 A1 | 9/2004 | Sullivan et al. |
| 2004/0176913 A1 | 9/2004 | Kawatahara et al. |
| 2004/0186357 A1 | 9/2004 | Soderberg et al. |
| 2004/0186362 A1 | 9/2004 | Brauker et al. |
| 2004/0193090 A1 | 9/2004 | Lebel et al. |
| 2004/0195284 A1 | 10/2004 | Iitsuka |
| 2004/0199059 A1 | 10/2004 | Brauker et al. |
| 2004/0200867 A1 | 10/2004 | Chee |
| 2004/0204863 A1 | 10/2004 | Kim et al. |
| 2004/0210458 A1 | 10/2004 | Evans et al. |
| 2004/0232180 A1 | 11/2004 | Badillo |
| 2004/0260155 A1 | 12/2004 | Ciarniello et al. |
| 2005/0003470 A1 | 1/2005 | Nelson et al. |
| 2005/0023137 A1 | 2/2005 | Bhullar et al. |
| 2005/0031689 A1 | 2/2005 | Shults et al. |
| 2005/0038680 A1 | 2/2005 | McMahon |
| 2005/0043598 A1 | 2/2005 | Goode, Jr. et al. |
| 2005/0045685 A1 | 3/2005 | Sesto |
| 2005/0048194 A1 | 3/2005 | Shmulewitz |
| 2005/0055243 A1 | 3/2005 | Arndt et al. |
| 2005/0059873 A1 | 3/2005 | Glozman et al. |
| 2005/0065555 A1 | 3/2005 | Er |
| 2005/0071752 A1 | 3/2005 | Marlatt |
| 2005/0090607 A1 | 4/2005 | Tapsak et al. |
| 2005/0092791 A1 | 5/2005 | Labarca et al. |
| 2005/0112169 A1 | 5/2005 | Brauker et al. |
| 2005/0131311 A1 | 6/2005 | Leuthardt et al. |
| 2005/0143635 A1 | 6/2005 | Kamath et al. |
| 2005/0154271 A1 | 7/2005 | Rasdal et al. |
| 2005/0171512 A1 | 8/2005 | Flaherty |
| 2005/0176136 A1 | 8/2005 | Burd et al. |
| 2005/0182366 A1 | 8/2005 | Vogt et al. |
| 2005/0187720 A1 | 8/2005 | Goode, Jr. et al. |
| 2005/0192557 A1 | 9/2005 | Brauker et al. |
| 2005/0203461 A1 | 9/2005 | Flaherty et al. |
| 2005/0203707 A1 | 9/2005 | Tsutsui et al. |
| 2005/0238507 A1 | 10/2005 | DiIanni et al. |
| 2005/0239156 A1 | 10/2005 | Drucker et al. |
| 2005/0245795 A1 | 11/2005 | Goode, Jr. et al. |
| 2005/0245799 A1 | 11/2005 | Brauker et al. |
| 2005/0256417 A1 | 11/2005 | Rischell et al. |
| 2005/0260174 A1 | 11/2005 | Fraser et al. |
| 2005/0261558 A1 | 11/2005 | Eaton et al. |
| 2005/0267780 A1 | 12/2005 | Ray et al. |
| 2005/0271996 A1 | 12/2005 | Sporbert et al. |
| 2005/0277164 A1 | 12/2005 | Drucker et al. |
| 2005/0281706 A1 | 12/2005 | Funke et al. |
| 2005/0283386 A1 | 12/2005 | Powers et al. |
| 2005/0288571 A1 | 12/2005 | Perkins et al. |
| 2006/0004603 A1 | 1/2006 | Peterka et al. |
| 2006/0004607 A1 | 1/2006 | Marshall et al. |
| 2006/0010098 A1 | 1/2006 | Goodnow et al. |
| 2006/0015020 A1 | 1/2006 | Neale et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0031094 A1 | 2/2006 | Cohen et al. |
| 2006/0036134 A1* | 2/2006 | Tarassenko et al. .......... 600/300 |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0041229 A1 | 2/2006 | Garibotto et al. |
| 2006/0051738 A1 | 3/2006 | Zweig |
| 2006/0058612 A1 | 3/2006 | Dave et al. |
| 2006/0058626 A1 | 3/2006 | Weiss et al. |
| 2006/0063135 A1 | 3/2006 | Mehl |
| 2006/0094952 A1 | 5/2006 | Ma et al. |
| 2006/0095225 A1 | 5/2006 | Harmon et al. |
| 2006/0115790 A1 | 6/2006 | Alon et al. |
| 2006/0129328 A1 | 6/2006 | Leo et al. |
| 2006/0143041 A1 | 6/2006 | Tipirneni |
| 2006/0167718 A1 | 7/2006 | Tischer |
| 2006/0173444 A1 | 8/2006 | Choy et al. |
| 2006/0178633 A1 | 8/2006 | Garibotto et al. |
| 2006/0222566 A1 | 10/2006 | Brauker et al. |
| 2006/0224141 A1 | 10/2006 | Rush et al. |
| 2006/0226985 A1 | 10/2006 | Goodnow et al. |
| 2006/0235009 A1 | 10/2006 | Glickman et al. |
| 2006/0240549 A1 | 10/2006 | Minton |
| 2006/0241969 A1 | 10/2006 | Wilhide et al. |
| 2006/0244465 A1 | 11/2006 | Kroh et al. |
| 2006/0247710 A1 | 11/2006 | Goetz et al. |
| 2006/0272652 A1 | 12/2006 | Stocker et al. |
| 2006/0282290 A1 | 12/2006 | Flaherty et al. |
| 2006/0287691 A1 | 12/2006 | Drew |
| 2007/0012324 A1 | 1/2007 | Nirkondar et al. |
| 2007/0016381 A1 | 1/2007 | Kamath et al. |
| 2007/0016449 A1 | 1/2007 | Cohen et al. |
| 2007/0033074 A1 | 2/2007 | Nitzan et al. |
| 2007/0033114 A1 | 2/2007 | Minor |
| 2007/0041626 A1 | 2/2007 | Weiss et al. |
| 2007/0061170 A1 | 3/2007 | Lorsch et al. |
| 2007/0067000 A1 | 3/2007 | Strother et al. |
| 2007/0074043 A1 | 3/2007 | Lacey |
| 2007/0096715 A1 | 5/2007 | Joy et al. |
| 2007/0100215 A1 | 5/2007 | Powers et al. |
| 2007/0118405 A1 | 5/2007 | Campbell et al. |
| 2007/0149861 A1 | 6/2007 | Crothall et al. |
| 2007/0156033 A1 | 7/2007 | Causey, III et al. |
| 2007/0163880 A1 | 7/2007 | Woo et al. |
| 2007/0173698 A1 | 7/2007 | Kivela et al. |
| 2007/0185390 A1 | 8/2007 | Perkins et al. |
| 2007/0203966 A1 | 8/2007 | Brauker et al. |
| 2007/0219432 A1 | 9/2007 | Thompson |
| 2007/0219480 A1 | 9/2007 | Kamen et al. |
| 2007/0219597 A1 | 9/2007 | Kamen et al. |
| 2007/0235331 A1 | 10/2007 | Simpson et al. |
| 2007/0244383 A1 | 10/2007 | Talbot et al. |
| 2007/0255531 A1 | 11/2007 | Drew |
| 2007/0258395 A1 | 11/2007 | Jollota et al. |
| 2007/0293932 A1 | 12/2007 | Zilla et al. |
| 2008/0004904 A1 | 1/2008 | Tran |
| 2008/0021666 A1 | 1/2008 | Goode, Jr. et al. |
| 2008/0026338 A1 | 1/2008 | Cinader |
| 2008/0030369 A1 | 2/2008 | Mann et al. |

| | | |
|---|---|---|
| 2008/0033254 A1 | 2/2008 | Kamath et al. |
| 2008/0045824 A1 | 2/2008 | Tapsak et al. |
| 2008/0062891 A1 | 3/2008 | Van der Merwe et al. |
| 2008/0063948 A1 | 3/2008 | O'Brien |
| 2008/0064943 A1 | 3/2008 | Talbot et al. |
| 2008/0065236 A1 | 3/2008 | Bristol |
| 2008/0071156 A1 | 3/2008 | Brister et al. |
| 2008/0071328 A1 | 3/2008 | Haubrich et al. |
| 2008/0071580 A1 | 3/2008 | Marcus et al. |
| 2008/0073993 A1 | 3/2008 | Sortore et al. |
| 2008/0077433 A1 | 3/2008 | Kasprisin et al. |
| 2008/0078567 A1 | 4/2008 | Miller et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0105748 A1 | 5/2008 | Lei |
| 2008/0105749 A1 | 5/2008 | Lei |
| 2008/0108942 A1 | 5/2008 | Brister et al. |
| 2008/0119705 A1 | 5/2008 | Patel et al. |
| 2008/0126882 A1 | 5/2008 | Fulton et al. |
| 2008/0129465 A1 | 6/2008 | Rao |
| 2008/0145277 A1 | 6/2008 | Wohland |
| 2008/0183061 A1 | 7/2008 | Goode et al. |
| 2008/0183399 A1 | 7/2008 | Goode et al. |
| 2008/0183500 A1 | 7/2008 | Banigan |
| 2008/0188731 A1 | 8/2008 | Brister et al. |
| 2008/0189051 A1 | 8/2008 | Goode et al. |
| 2008/0194935 A1 | 8/2008 | Brister et al. |
| 2008/0194936 A1 | 8/2008 | Goode et al. |
| 2008/0194937 A1 | 8/2008 | Goode et al. |
| 2008/0194938 A1 | 8/2008 | Brister et al. |
| 2008/0195232 A1 | 8/2008 | Carr-Brendel et al. |
| 2008/0195967 A1 | 8/2008 | Goode et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0235469 A1 | 9/2008 | Drew |
| 2008/0242961 A1 | 10/2008 | Brister et al. |
| 2008/0255438 A1 | 10/2008 | Saidara et al. |
| 2008/0262469 A1 | 10/2008 | Brister et al. |
| 2008/0275313 A1 | 11/2008 | Brister et al. |
| 2008/0281167 A1 | 11/2008 | Soderberg et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0306368 A1 | 12/2008 | Goode et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2008/0312518 A1 | 12/2008 | Jina et al. |
| 2009/0005666 A1 | 1/2009 | Shin et al. |
| 2009/0007237 A1 | 1/2009 | Lorsch |
| 2009/0012379 A1 | 1/2009 | Goode et al. |
| 2009/0018424 A1 | 1/2009 | Kamath et al. |
| 2009/0018779 A1 | 1/2009 | Cohen et al. |
| 2009/0030294 A1 | 1/2009 | Petisce et al. |
| 2009/0030733 A1 | 1/2009 | Cohen et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048501 A1 | 2/2009 | Goodnow |
| 2009/0062633 A1 | 3/2009 | Brauker et al. |
| 2009/0062635 A1 | 3/2009 | Brauker et al. |
| 2009/0069744 A1 | 3/2009 | Goodnow |
| 2009/0076356 A1 | 3/2009 | Simpson et al. |
| 2009/0076360 A1 | 3/2009 | Brister et al. |
| 2009/0076361 A1 | 3/2009 | Kamath et al. |
| 2009/0085768 A1 | 4/2009 | Patel et al. |
| 2009/0088427 A1 | 4/2009 | Clickman et al. |
| 2009/0099436 A1 | 4/2009 | Brister et al. |
| 2009/0112478 A1 | 4/2009 | Mueller, Jr. et al. |
| 2009/0124877 A1 | 5/2009 | Goode, Jr. et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0150186 A1 | 6/2009 | Cohen et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0221880 A1 | 9/2009 | Soderberg et al. |
| 2009/0224773 A1 | 9/2009 | Joy et al. |
| 2009/0224837 A1 | 9/2009 | Joy et al. |
| 2009/0227876 A1 | 9/2009 | Tran et al. |
| 2009/0227877 A1 | 9/2009 | Tran et al. |
| 2009/0228304 A1 | 9/2009 | Ciarniello et al. |
| 2009/0240120 A1 | 9/2009 | Mensinger et al. |
| 2009/0240127 A1 | 9/2009 | Ray |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0258790 A1 | 10/2009 | Cohen et al. |
| 2009/0269315 A1 | 10/2009 | Fraser et al. |
| 2009/0273353 A1 | 11/2009 | Kroh et al. |
| 2009/0278553 A1 | 11/2009 | Kroh et al. |
| 2009/0281519 A1 | 11/2009 | Rao et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0063373 A1 | 3/2010 | Kamath et al. |
| 2010/0076283 A1 | 3/2010 | Simpson et al. |
| 2010/0081908 A1 | 4/2010 | Dobbles et al. |

| | | | |
|---|---|---|---|
| 2010/0081910 | A1 | 4/2010 | Brister et al. |
| 2010/0087724 | A1 | 4/2010 | Brauker et al. |
| 2010/0088119 | A1 | 4/2010 | Tipirneni |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0119693 | A1 | 5/2010 | Tapsak et al. |
| 2010/0121169 | A1 | 5/2010 | Petisce et al. |

FOREIGN PATENT DOCUMENTS

| | | |
|---|---|---|
| JP | 2002-523149 | 7/2002 |
| WO | WO-00/10628 | 3/2000 |
| WO | WO-02/41231 | 5/2002 |
| WO | WO-03/049597 | 6/2003 |
| WO | WO-2004/110256 | 12/2004 |
| WO | WO-2005/040793 | 5/2005 |
| WO | WO-2005/119524 | 12/2005 |
| WO | WO-2006/026741 | 3/2006 |
| WO | WO-2006/069657 | 7/2006 |
| WO | WO-2006/086423 | 8/2006 |

OTHER PUBLICATIONS

International Preliminary Report on Patentability for PCT Application No. PCT/US2004/018204 filed Jun. 4, 2004.
Supplementary European Search Report for EP Application No. EP-04754727 filed Jun. 4, 2004.
Travenol Laboratories, Inc., *An Introduction to "Eugly"*, Book 1, 1985, pp. 1-22.
Canadian Patent Application No. 2,528,832, Examiner's Report mailed Mar. 29, 2011.
Japanese Patent Application No. 2006-533619, English Translation & Original Language of Office Action mailed Dec. 22, 2009.
Japanese Patent Application No. 2006-533619, English Translation & Original Language of Office Action mailed Dec. 24, 2010.
Canadian Patent Application No. 2,528,832, Examiner's Report mailed Oct. 27, 2011.
European Patent Application No. EP-04754727, Official Letter mailed Jan. 13, 2012.
Berndt, D. J., et al., "Introduction to the Minitrack: Databases, Data Warehousing, and Data Mining in Health Care", *System Sciences, Proceedings of 33rd Annual Hawaii International Conference on* Jan. 4-7, 2000, pp. 1588-1588.
U.S. Appl. No. 12/239,022, Notice of Allowance mailed Aug. 11, 2010.
U.S. Appl. No. 12/239,022, Office Action mailed Jan. 27, 2010.
U.S. Appl. No. 12/239,022, Office Action mailed May 14, 2009.

* cited by examiner

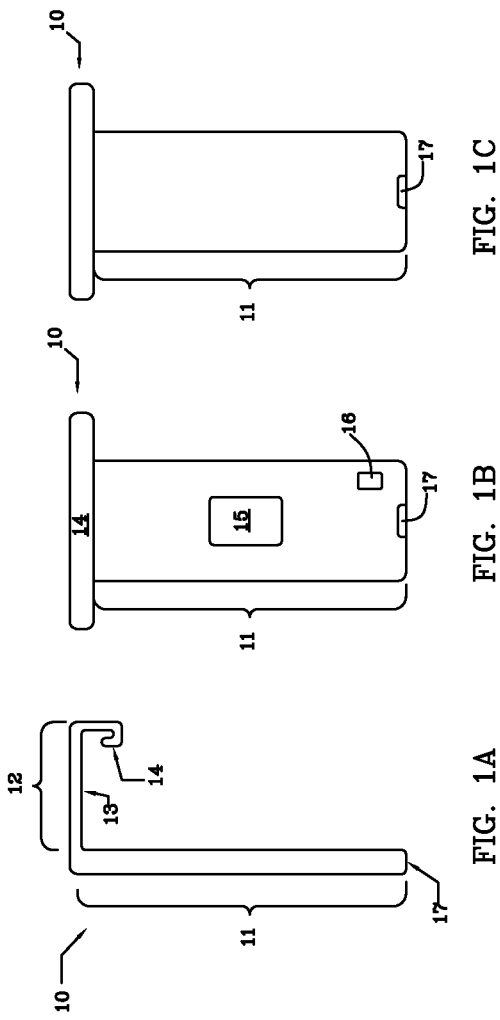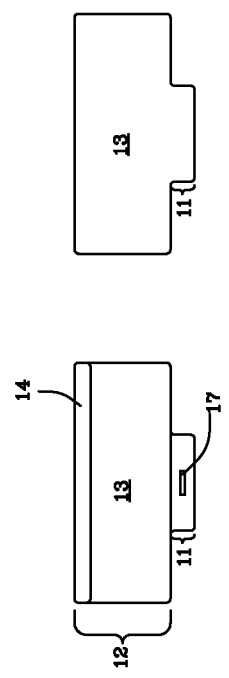

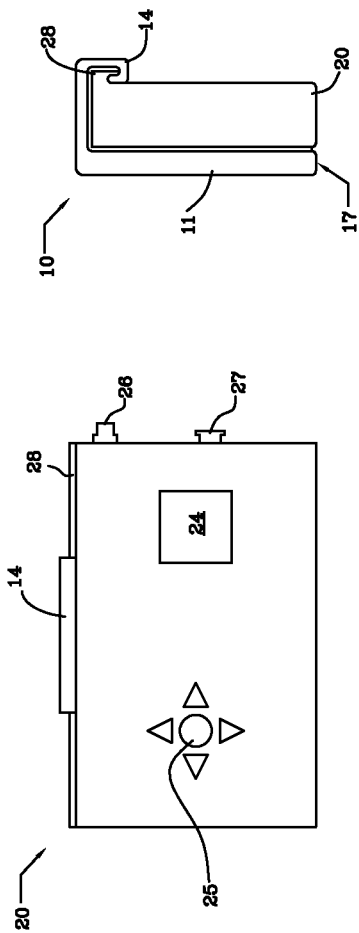
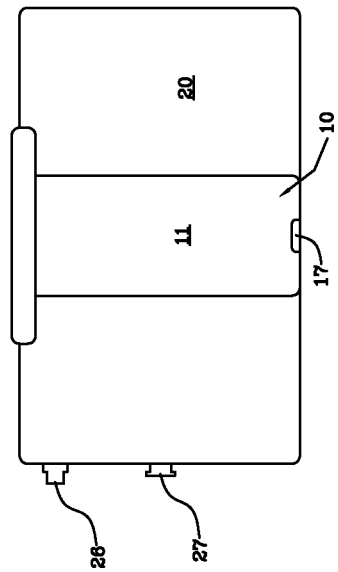
FIG. 3A
FIG. 3B
FIG. 3C

GLUCOSE MEASURING MODULE AND INSULIN PUMP COMBINATION

FIELD OF THE INVENTION

This invention relates to a device and method by which a glucose reading from a detachable portable glucose sensor module can be wirelessly delivered to an insulin pump on which the module is mounted.

BACKGROUND

The number of diagnosed cases of diabetes continues to increase in the U.S. and throughout the world, creating enormous economic and public health consequences. Devices and therapies that improve the quality of life for the diabetic patient thus are important not only for the patient, but for society at large. One area in which recently developed technologies have been able to improve the standard of care has been in the maintenance of tight control over the blood glucose levels. It is well known that if a diabetic patient's blood glucose values can be maintained in a relatively narrow and normal range of from about 80 milligrams per deciliter (mg/dL) to about 120 mg/dL, the physiologically damaging consequences of unchecked diabetes can be minimized. With better blood glucose information, diabetic patients can better exercise tight control of their blood glucose level through a variety of means, including diet, exercise, and medication. For this reason a large industry has developed to provide the diabetic population with even more convenient and accurate ways to measure blood glucose. There are many forms of these measuring devices; one common type is represented by hand-held electronic meters which receive blood samples via enzyme-based "test strips". In using these systems, the patient lances a finger or alternate body site to obtain a blood sample, the strip is inserted into a test strip opening in the meter housing, the sample is applied to the test strip and the electronics in the meter convert a current generated by the enzymatic reaction in the test strip to a blood glucose value.

Some diabetic patients require insulin for the treatment of their diabetes, in order to maintain their glucose levels within the desired range. These "insulin-dependent" diabetic patients have traditionally administered insulin doses to themselves via a hypodermic syringe or with a specialized injector known as an "insulin pen". Although these injection methods can deliver insulin at an appropriate time and at an appropriate total dosage, the single bolus aspect of the delivery is unlike a physiological profile of insulin production in the body, which involves a lower rate of insulin entry into the bloodstream, over a more extended time course. A more recently available technology is represented by insulin pumps. These devices offer significant therapeutic value as they deliver insulin in a more physiological manner, with measured doses of insulin being infused slowly, over an extended period of time. Further, the rate at which insulin is delivered can be programmed to follow standard or individually-modified protocols, to give the user even better glucose control over the course of a day. Insulin pumps have commercially evolved to become small in size, which offers easier portability and unobtrusiveness, and with electronic advances, they have evolved to become more fully-featured, and thereby capable of enhanced performance. These various advantages in terms of health care quality and user convenience have supported the growth of the insulin pump market.

Diabetics and especially insulin pump users typically carry with them a strip-and-meter glucose test kit at all times, so they can ascertain their blood glucose level during their day. It has been recognized that combining the newer technologies of insulin administration with the newer technologies of glucose measurement could provide user convenience. Such an integrated combination is shown in U.S. Pat. No. 5,665,065, which teaches that the mechanism for measuring blood glucose can be built into the housing of an insulin pump. This patent further teaches that the combined glucose measuring and pump system can permit the user to (1) obtain a glucose value, (2) input the glucose value to the microprocessor based electronics within the pump housing, (3) direct the electronics to calculate a recommended modification to the default or currently in-use insulin delivery protocol, and (4) select either the newly recommended protocol or the original default insulin delivery protocol.

While the advantages of such glucose measuring/insulin pump combinations have been known in the patent literature for many years, in fact, no such device has become commercially available. One fundamental reason for this concept remaining unrealized in the market may involve the now standard and expected watertight feature of the pump, which allows the pump user to shower and swim without removing the pump. On the other hand, waterproofing of a glucose strip testing device is inherently problematic, as the strip port itself is a necessary open connection between the space within the glucose sensing device and the external environment. Thus, the full integration of glucose strip test functionality into an insulin pump would remove the desirable watertight feature of the pump. Such would be the case with a device according to the type shown in U.S. Pat. No. 5,665,065, which if exposed to a wet environment, would allow the entry of water through the test strip opening in the pump housing, where the water could damage the electronics and/or mechanical portions of the pump.

Other practical factors may also contribute to the failure of a combination device to enter the market. Insulin pumps, though expensive, are becoming well established in the market. Pump users tend to remain loyal to their initial choice. Glucose meters, in contrast, are less expensive to acquire (they are often provided to users without charge), and users more often switch between meter brands. Thus, in designing such an integrated combination device, a pump manufacturer would need to commit to particular blood glucose measuring technology in the face of the concern that such technology could become less competitive or even obsolete during the normal life of the pump product. Finally, pump manufacturers are very aware that pump users are interested in pumps that are small and unobtrusive. Clearly, combining two devices can only increase the size of the pump housing, thus making the pump potentially less attractive in a market that has become used to the idea that smaller is better.

In view of these various technical factors associated with the therapeutic devices and the market considerations, it would be desirable to provide an insulin pump user the benefits and performance of a functionally combined glucose measuring device and insulin pump in a configuration that nevertheless avoids the practical disadvantages associated with a physical integration.

SUMMARY OF THE INVENTION

A combination glucose measuring and insulin pumping device in which two major components, a glucose measuring module and an insulin pump, are held together by a quick attach and release mechanism. Communication between the glucose measuring module and the insulin pump is by a wireless modality. The glucose measuring module determines the glucose level in a sample, and wirelessly transmits the data to the insulin pump, where the data is stored in a memory, and is available for visual display on the insulin pump, and for incorporation into selection of appropriate protocols for the rate of insulin infusion by the pump into the patient.

The invention features a glucose measuring module that includes glucose measuring circuitry preferably for enzymatic electrochemical detection of glucose in a blood sample. The module includes a quick attach and release clasp permitting the user to readily attach and detach the module from an insulin pump housing. The module further includes circuitry for wirelessly transmitting data related to the glucose values determined in the module to the attached insulin pump, for example by infrared radiation. The module can be inexpensively manufactured since it need not include a display or control buttons, but can, instead, rely on the controls and display on the insulin pump.

BRIEF DESCRIPTION OF THE DRAWINGS

The invention will now be described by reference to the figures, wherein like reference numerals and names indicate corresponding structure throughout the several views.

FIGS. 1A-1E show the glucose measuring module of the invention in a side view, front view, back view, bottom view, and top view, respectively.

FIGS. 3A-3C show the combined glucose measuring module and insulin pump housing combination in a front view, side view, and back view, respectively.

DETAILED DESCRIPTION

Figure 2:
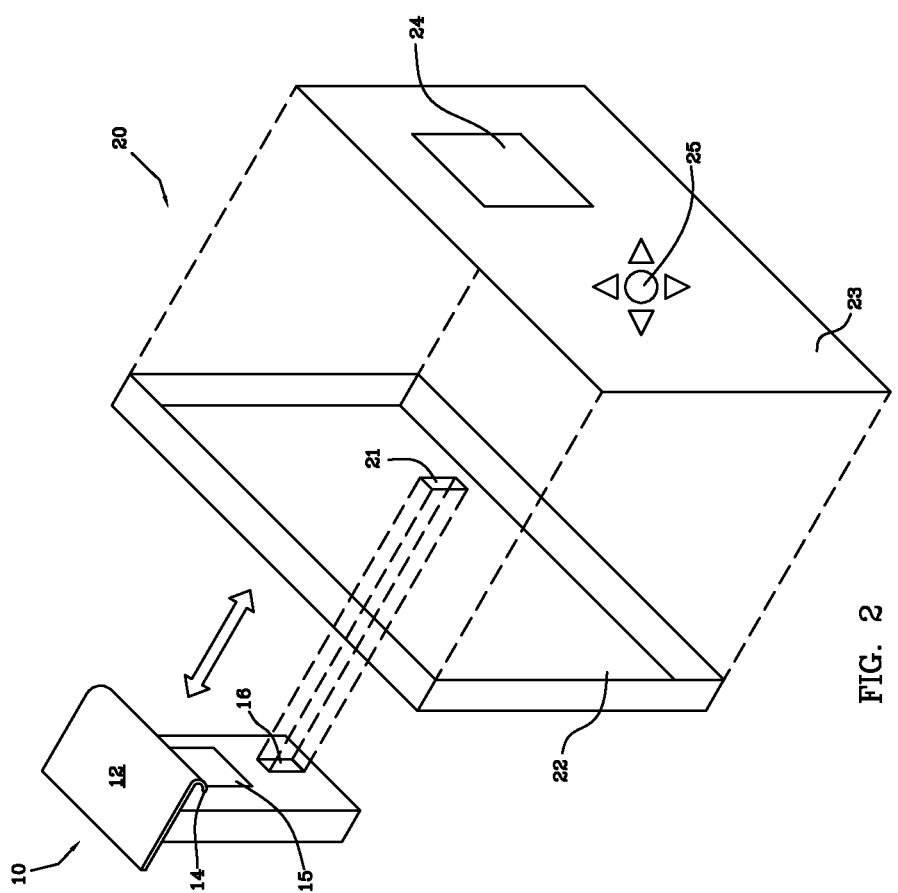
FIG. 2 shows a perspective view of the glucose measuring module separate from, but in relation to, an insulin pump housing. In this view the insulin pump housing is shown exploded forward from the back of the housing to expose an interior side of the back wall.

The present invention is a device resulting from the functional combination of a glucose measuring device and an insulin pump, wherein the device and pump are connected by a quick attach and release mechanism. By way of an overview of the figures, FIGS. 1A-1E depict the glucose measuring device or module portion of the combination in various views; FIG. 2 depicts the glucose measuring component and the insulin pump component device aligned with respect to each other as they are positioned for attachment together; and FIGS. 3A-3C depict the two major device components, the glucose sensor and the insulin pump housing, in their mutually attached or coupled configuration, in various views.

In the invention, the glucose measuring device determines a user's glucose level (typically from a sample of blood), and wirelessly transmits that information to the insulin pump. The insulin pump, in turn, receives the wirelessly transmitted data, and through a microprocessor, places the data in memory for storage, and from the memory the data can be sent to a display, and/or can be utilized in controlling the performance of the pump. By way of noting design requirements and constraints on the invention, it is important that the glucose measuring device portion of the invention is as small as possible, and specifically shaped in such a way as to minimize the size of the combined measuring device and pump combination. It is within the scope of the invention that the measuring device, in a preferred embodiment, need not include a display. In this manner the device can be less expensively manufactured, and its size minimized. However, in combination with the pump, the data delivered to the pump from the measuring device can be displayed on the existing pump display. While the module need not include a large or expensive display, it may nevertheless be advantageous to include some ability to advise the user of a glucose level which is determined when the module is used as a "stand-alone" unit. For example, the module could include a very low cost, small three digit LCD display. Alternatively, the module could include LED indicator lights (e.g. red for out of desired range, green for within desired range).

FIGS. 1A-1E depict a glucose measuring module 10 comprising a glucose sensor housing 11 and a quick attach/quick release clasp 12. The clasp can be made of a variety of materials, including metal or plastic, or parts including both. In a preferred form, clasp 12 includes an extension portion 13, which portion extends across the top of an insulin pump housing (as seen in FIGS. 2 and 3), and a lip/connector portion 14.

FIG. 1A shows the glucose measuring device in a side view and highlights the thin profile of housing 11. Test strip port 17 can also be seen at the bottom of the module. Clasp 12 is seen in this embodiment to be integrated with and contiguous with the glucose sensor housing 11. Alternatively, all or a portion of clasp 12 can form part of the insulin pump housing and nevertheless form a connection with housing 11 when module 10 and the insulin pump housing are brought together. In yet another form of the invention, clasp 12 can be a part separate from, but attachable to, both module housing 11 and the insulin pump housing.

Glucose sensor housing 11 contains any glucose sensing system of the type well known in the art that can be configured to fit into a small and preferably thin profile. Such a system can include, for example, the electrochemical glucose strip and meter sensing system sold by Abbott Diabetes Care Inc. of Alameda, Calif. under the FreeStyle® brand, or other strip and meter glucose measuring systems. The housing thus encompasses the sensor electronics and strip connector (not shown), which connector is accessed via test strip port 17. Housing 11 will typically also include a battery or batteries which are accessed via battery door 15. In a preferred form of the invention, housing 11 includes a wireless data transmission port 16. Battery door 15 and data transmission port 16 have outer surfaces that are smoothly aligned with a matching surface of the housing, as shown in FIG. 1B (and the profile of FIG. 1A), so that housing 11 fits in an aligned fashion with the insulin pump housing to which it will be attached.

It is not necessary that the combination of the invention include a port for the transmission of infrared radiation, for example the data to be sent from the glucose sensing module to the pump can be transmitted by other known communications protocols such as Bluetooth®, IEEE 802.11b or other wireless protocols. It is important in the invention, however, that the data be sent in a manner that avoids having a "hard" or wired connection between the module and the pump housing so that it is not necessary to have a potentially water accessible opening in the pump housing. That is, the invention is most advantageously used with a pump having a housing that is "closed" in the sense that it is at least water-resistant and preferably is water-proof.

As will be described in detail below, the glucose sensing system in housing 11 is electronically activated by connection of a glucose test strip to the glucose sensing system via test strip port 17. Alternatively, the sensing system can be activated by on/off buttons that can be incorporated into the housing as is common with glucose meters. However, the preferred embodiment depicted in FIGS. 1-3 does not have manual control buttons on the glucose sensing module housing. Thus, in this embodiment, control of the function of the glucose sensing module is undertaken via the user accessible control buttons on the pump housing in combination with the pump and module microprocessors.

In a front view (FIG. 1B) of glucose measuring module 10, the relative width and breadth of housing 11 is evident. Shown on the inner or front face of housing 11 are battery door 15 and wireless data transmission port 16. The wireless transmission mode in this embodiment is infrared (IR). In a back view (FIG. 1C) of glucose measuring module 10, the shape of housing 11 and extension portion 13 of quick attach and release clasp 12 is shown. The bottom view of FIG. 1D of module 10 shows the position of strip port opening 17 relative to housing 11. FIG. 11E shows the upper aspect of sensor housing 11 as it connects with extension portion 13.

Clasp 12 is of a quick attach and release type for detachably coupling glucose measuring module 10 to insulin pump housing 20 (see FIG. 2 below). Terms synonymous to "quick attach and release" include "quick-connect", "snap-on", "snap-fit" and "click-on". The connection afforded by clasp 12 has a mechanical stability that is sufficient to ensure that the two component devices remain coupled during normal use, and sufficient to maintain the stability and alignment of the IR wireless connection between data transmission port 16 of the module and an IR data receiver port 21 of the insulin pump. The attachment and detachment of these components via the clasp is of a quick and simple nature, requiring neither tools nor manual exertion beyond finger force to effect. Further, preferably, the connection and disconnection steps are each single-action in nature; connection need not be followed by a locking step, nor is disconnection preceded by any required unlocking step.

In the presently described and illustrated embodiment, clasp 12 is integrally associated with the glucose sensor module 10, and it actively clasps insulin pump housing 20. As mentioned, however, the clasp can instead be integrally associated with pump housing 20, from which position it clasps module 10. Alternatively, the clasp can be a stand-alone piece, integrally associated with neither the glucose sensor module nor the insulin pump, but capable of clasping and binding the two component devices together. The depicted clasp embodiment and the alternatives described are but examples of numerous variations of quick attach and release mechanisms that are well known in the art, and would be functionally equivalent to the examples illustrated and described herein. For example, it may be useful to use protrusions on pump housing 20 for engagement of the module/clasp. In particular, one or both of the fitting for the insulin infusion set and the battery cap (shown as 26 and 27 in FIG. 3, respectively) may be used as anchors for such engagement.

Returning to the figures in sequence, FIG. 2 shows the combination glucose measuring device and insulin pump, exploded and in a perspective view, with the internal mechanisms and electronics of the pump not appearing for clarity. An embodiment of glucose sensor module 10 and an exemplary insulin pump housing 20 are shown obliquely from their front, aligned in their mutually attached configuration, but exploded outward from each other. From this front view perspective, battery receptacle door 15 and IR transmission port 16 of glucose module 10 are visible, as well as clasp 12 with its extension portion 13 (FIG. 1A) and lip portion 14. Insulin pump housing 20 includes a back wall 22 and a front or face wall 23. This view shows the back and front walls exploded apart from each other in order to expose the interior aspect of back wall 22, thus showing the position of wireless data receiver port 21 contained therein. It is further illustrated in FIG. 2 that wireless data transmission port 16 of glucose sensor module 10, and the wireless data receiver port 21 of insulin pump housing 20 are physically aligned in a manner such that when the glucose sensor module and the insulin pump are clasped together in the configuration of the combined device that the two wireless ports are directly facing each other. Such direct alignment is appropriate in order to support robust wireless transmitting and receiving of data in the IR spectral range.

Visible on the front face wall of housing 20 are visual display 24, and pump control buttons 25. These control buttons are also used to manage the glucose sensor module as well, when the module is clasped to the housing and in alignment for IR communication. Though wireless communication can be accomplished via means (such as Bluetooth®) that do not require such alignment, the present embodiment must have a clasp that ensures such alignment. This can be accomplished by including limits or "stops" (not shown) to the width of the lip engaging portion 28 (FIG. 3B) on housing 20 to which lip 14 of module 10 engages, so as to permit attachment of the module only in a position in which there is alignment.

Insulin pump housing 20 is preferably "watertight," to protect the internal mechanisms and electronics from the damaging effects of water. "Watertightness" refers to the prevention of water ingress into an article or piece of equipment under various conditions of water exposure. To quantify the degree of watertightness, the Japanese Industrial Standards and the British Standards both use a scale that ranges from "0" to "8", and the definitions of each level in both systems are very similar to each other. To clarify, what is being quantified is the level of water exposure, not the degree to which water is excluded (which is absolute). The watertightness of the insulin pump housing is preferably in compliance with level 8 of both the Japanese and British standards. Thus, "JIS 8" (Japanese Industrial Standards) and "IPX8" (British Standards Institute, Water Intrusion Standards) define watertightness in a submersion context, i.e., the equipment excluding water while being continually submerged (or immersed) in water for periods of time and at depths or pressures that are specified by the manufacturer. A typical level 8 specification for the watertightness of an insulin pump housing is, for example, watertightness when submerged to a depth of 8 feet for 30 minutes, or to a depth of 12 feet for 3 minutes.

FIGS. 3A-3C show the combination glucose measuring module and insulin pump in a front view (FIG. 3A), side view (FIG. 3B), and back view (FIG. 3C). The front view shows the functional or interactive face of the insulin pump, where visual display 24 and control buttons 25 are located. These display and control elements represent the device user interface, where the diabetic patient can view glucose sensor information, and control the performance of the insulin pump and the glucose sensing system. On one lateral side of the pump, in this embodiment, is a fitting 26 for an insulin infusion line, as is well known, and a screw type battery cover 27. Visible in the front and side views is lip engaging portion 28. Side view (FIG. 3B) is redundant of FIG. 1A with respect to the glucose measuring module 10, but shows insulin pump housing 20 also, as well as the attached or coupled form of the combined glucose module and insulin pump. The back view (FIG. 3C) shows the back of glucose measuring module 10 in the foreground, and the back of the insulin pump 20 in the background. Glucose sensor module 10, the module's strip port 17, and the clasp portion of the glucose measuring device are apparent, as depicted earlier in FIG. 1C. Visible on the left side of pump housing 20, in this back view, is fitting 26 for the insulin infusion line as well as battery cover 27, as was shown also in FIG. 3A.

With regard to the wireless communication between glucose measuring module 10 and the insulin pump, as noted above, the modality is infrared (IR) light, preferably transmitted using IRDA Data Protocols. This modality is appropriate for high-speed, short-range, line-of-sight, point-to-point wireless data transfer. Features of infrared data transmission are well described on the website of the Infrared Data Association (http://www.irda.org/). IrDA Data defines a standard for an interoperable universal two-way wireless IR transmission port. The technology is widespread, being installed within more than 300 million electronic devices, many of which are of the portable or handheld variety, including insulin pumps such as the Deltec Cozmo™ pump, made by Deltec, Inc. (St. Paul, Minn.).

In the context of the present invention, to review, wireless data are transferred between the glucose measuring module via data transmission port 16 and data receiver port 21 of the insulin pump, which are aligned in close apposition when the glucose measuring module and the insulin pump are attached together in the configuration of the invention. These data ports are two-way transceivers, they are termed "transmission" (in the case of the glucose measuring module port) and "receiver" (in the case of the insulin pump) because of the predominant direction of signal flow, which is from the glucose measuring module to the insulin pump. In practice, however, there is transmission of some information back from the insulin pump to the glucose measuring module, which is important particularly in establishing a secure, mutual, and specific recognition between the individual components.

In practice, the inventive combination glucose measuring and insulin pump device is operated in the manner now to be described briefly. A typical user of this invention would be an insulin dependent diabetic, who is using an insulin-infusion pump, and who checks his or her blood glucose level multiple times per day. First, the patient assures that the glucose measuring device and the insulin pump are properly attached or coupled to each other, and then inserts a glucose test strip into strip port 17 of glucose measuring module 10. Within the glucose measuring module, the connection of the strip with a glucose strip connector (not shown) provides an electrical connection between the strip and the internal electronics of the module. Upon such contact between the glucose strip and the glucose strip connector, software within the module and pump is activated (either without specific user interaction via connection between conductive portions of the strip and the connector, or manually using control buttons 25 on the pump) in order to be ready to receive electrical data from the glucose test strip. Activation of the glucose measuring module causes electronics within the module to transmit a signal through the wireless transmission port 16, which is, in turn, received through the data receiver port 21 of the insulin pump, and such activation is noted on display 24 of the pump. The opposite end of the glucose strip remains protruding out from the glucose module.

Next, the patient obtains a small volume blood sample through the use of a skin puncturing device or lancet. Details of the operation of the lancet and the glucose level determining procedures are well described in U.S. Pat. Nos. 6,143,164 and 6,338,790, incorporated herein by reference. The patient then brings an exposed edge of the glucose test strip into contact with the blood drop that has appeared at the lancet puncture site, and the blood moves into a sample chamber within the glucose strip. Electronic mechanisms within the test strip sense when a sufficient sample volume is contained within the sample chamber, a signal is wirelessly transmitted from the glucose measuring module to the insulin pump, as described above, and a notice of this sufficient volume then appears on the display of the insulin pump. Electrochemical processes within the glucose test strip then proceed to determine the level of glucose in the sample, and such data is, in turn, wirelessly transmitted from the glucose module to the insulin pump, where the data is stored in an electronic memory, is displayed on the insulin pump display, and is available for retrieval at a later time and/or available for entering into other electronic processes that control the function of the insulin pump. Upon completion of data transfer, as indicated by information appearing on the pump display, the user withdraws the glucose test strip and discards it. According to particulars of the pump type and manufacturer, and particular methods of pump use, the user can then proceed to make use of the glucose data within the larger context of his or her medical care.

The invention has been described with reference to various specific and preferred embodiments and techniques. It will be apparent, however, to one of ordinarily skill in the art that many variations and modifications may be made while remaining within the spirit and scope of the invention.

What is claimed is:

1. A glucose sensor module, comprising:
an exterior glucose sensor module housing without a display, the exterior glucose sensor module housing including a strip port;
a glucose sensor strip connector coupled to the exterior glucose sensor module housing;
a microprocessor provided in the exterior glucose sensor module housing for receiving data from a glucose sensor strip via the connector and for determining data relating to a glucose value based on a sample on the glucose sensor strip;
a data communication module in signal communication with the microprocessor for receiving the data and transmitting the data from the glucose sensor module; and
a mechanical clasp including a lip shaped to permit removable attachment of the exterior glucose sensor module housing with a lip engaging portion of an insulin pump having a data port;
wherein when the mechanical clasp is removably attached with the lip engaging portion, the data communication module is aligned with the data port of the insulin pump to transfer data therebetween; and further
wherein the microprocessor is activated to initiate one or more routines to determine the data related to the glucose value based on the sample on the glucose sensor strip when the microprocessor detects a presence of the glucose sensor strip in the strip port.

2. The glucose sensor module of claim 1 wherein the data communication module comprises one of an infrared transmitter or a receiver or a short range radio frequency transmitter and/or receiver.

3. The glucose sensor module of claim 1 wherein the glucose test strip is an electrochemical enzymatic biosensor.

4. A glucose sensor module, comprising:
an exterior glucose sensor module housing without a display, the exterior glucose sensor module housing including a glucose sensor strip connector and a data communication port;
at least one microprocessor for receiving data from a glucose sensor strip via the glucose sensor strip connector and for determining data relating to a glucose value based on a sample on the glucose sensor strip;

a wireless data transmission module communicating with the at least one microprocessor for receiving the data and wirelessly transmitting the data; and a mechanical clasp shaped to permit removable attachment of the exterior glucose sensor module housing with an insulin pump in a single action;

wherein the data transmission module is configured to transmit the data when the exterior glucose sensor module housing is removably attached to the insulin pump such that the data communication port is in alignment with a communication port on the insulin pump.

5. The glucose sensor module of claim 4, wherein the wireless data transmission module comprises one of an infrared transmitter and/or receiver or a short range radio frequency transmitter and/or receiver.

6. The glucose sensor module of claim 4, wherein the glucose test strip is an electrochemical enzymatic biosensor.

7. The glucose sensor module of claim 4, wherein the mechanical clasp comprises a lip for engaging a lip-engaging portion on a housing of the insulin pump, so that insulin pump housing fits in an aligned fashion with the exterior glucose sensor module housing.

8. A glucose sensor module, comprising:

an exterior glucose sensor module housing without a display, the exterior glucose sensor module housing including a glucose sensor strip connector and a module data port;

a microprocessor coupled to the exterior glucose sensor module housing for receiving data from a glucose sensor strip via the glucose strip connector and for determining data relating to a glucose value based on a sample in the glucose sensor strip;

a wireless data transmission unit communicating with the microprocessor for receiving the data and wirelessly transmitting the data; and a mechanical clasp disposed on the exterior glucose sensor module housing and shaped to permit removable attachment of the exterior glucose sensor module housing with an insulin pump having a pump data port, wherein data relating to the glucose value are wirelessly transmitted from the module data port to the pump data port when the mechanical clasp removably attaches the exterior glucose sensor module housing to the insulin pump such that the pump data port and the module data port are aligned;

wherein the microprocessor is activated to initiate one or more routines to determine the data related to the glucose value based on the sample on the sensor strip when the microprocessor detects a presence of the sensor strip in the strip port.

9. The glucose sensor module of claim 8 wherein the wireless data transmission unit comprises one of an infrared transmitter and/or receiver or a short range radio frequency transmitter and/or receiver.

10. The glucose sensor module of claim 8 wherein the glucose test strip is an electrochemical enzymatic biosensor.

11. The glucose sensor module of claim 1 wherein the mechanical clasp extends, via an extension portion, from the exterior glucose sensor module housing.

12. The glucose sensor module of claim 11 wherein at least a portion of the extension portion is secured to at least a portion of a housing of the insulin pump when the mechanical clasp is removably attached to the lip engaging portion of the insulin pump.

13. The glucose sensor module of claim 1 wherein the lip engaging portion of the insulin pump includes at least one alignment mechanism configured to prevent the mechanical clasp from sliding along the lip engaging portion when the mechanical clasp is removably attached to the lip engaging portion of the insulin pump.

14. The glucose sensor module of claim 4 wherein the mechanical clasp extends, via an extension portion, from the exterior glucose sensor module housing.

15. The glucose sensor module of claim 14 wherein at least a portion of the extension portion is secured to at least a portion of a housing of the insulin pump when the mechanical clasp is removably attached to the insulin pump.

16. The glucose sensor module of claim 4 wherein the insulin pump includes at least one alignment mechanism configured to prevent the mechanical clasp from sliding along the insulin pump when the mechanical clasp is removably attached to the insulin pump.

17. The glucose sensor module of claim 8 wherein the mechanical clasp extends, via an extension portion, from the exterior glucose sensor module housing.

18. The glucose sensor module of claim 17 wherein at least a portion of the extension portion is secured to at least a portion of a housing of the insulin pump when the mechanical clasp is removably attached to the insulin pump.

19. The glucose sensor module of claim 8 wherein the insulin pump includes at least one alignment mechanism configured to prevent the mechanical clasp from sliding along the insulin pump when the mechanical clasp is removably attached to the insulin pump.

* * * * *